US00PP27621P2

(12) United States Plant Patent
Kordes

(10) Patent No.: US PP27,621 P2
(45) Date of Patent: Jan. 31, 2017

(54) FLORIBUNDA ROSE PLANT NAMED 'KORELAMBA'

(50) Latin Name: *Rosa hybrida*
Varietal Denomination: KORelamba

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 87 days.

(21) Appl. No.: 14/545,026

(22) Filed: Mar. 17, 2015

(51) Int. Cl.
*A01H 5/02* (2006.01)

(52) U.S. Cl.
USPC ..... Plt./141

(58) Field of Classification Search
USPC ..... Plt./150, 139, 108, 141, 151, 140, 148,Plt./149
See application file for complete search history.

(56) References Cited

PUBLICATIONS

New Plants and Flowers. Wine Red Bordaeux rose 2014, retrieved on Jul. 27, 2016, retrieved from the Internet at <http://www.newplantsandflowers.com/wine-red-bordaeux-rose/> 2 pp.*

* cited by examiner

*Primary Examiner* — June Hwu

(57) ABSTRACT

A new and distinct variety of rose with long lasting, novel wine-red flowers, and attractive foliage with very good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORelamba'.

CROSS REFERENCES AND FEDERAL R&D STATEMENT

There are no cross referenced or related applications.

FEDERAL R&D STATEMENT

This variety was developed without the aid of any research grant.

BACKGROUND OF THE INVENTION

The new variety of rose plant of the present invention originated from a controlled crossing in a breeding program of two distinct parents during the summer of 2004. The crossing was between an un-named seedling, the seed parent, and another un-named seedling, the pollen parent.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORelamba'.

'KORelamba' has not been made publically available or sold prior to one year before the date of this instant application. It was first offered for sale on Sep. 1, 2014 from the W. Kordes' Söhne Rosenschulen GmbH & Co KG, the inventor's nursery, in Klein Offenseth-Sparrieshoop, Germany. The first plants of the instant variety were available to the public on Sep. 15, 2014 as dormant bare root plants from the W. Kordes' Söhne Rosenschulen GmbH & Co KG, the inventor's nursery, in Klein Offenseth-Sparrieshoop, Germany.

SUMMARY OF THE INVENTION

The new rose plant may be distinguished from its seed parent, an un-named seedling, by the following combination of characteristics:

1. 'KORelamba' has large-sized flowers, whereas the un-named seedling has medium-sized flowers.
2. 'KORelamba' has a double petal count, whereas the un-named seedling has a semi-double petal count.

The new rose plant may be distinguished from its pollen parent, an un-named seedling, by the following combination of characteristics:

1. 'KORelamba' has an moderately upright growth habit, whereas the un-named seedling has a compact growth habit.
2. 'KORelamba' has a double petal count, whereas the un-named seedling has semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORelamba' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORelamba' was selected in May 2005 from the seedling beds to be asexually propagated for further evaluation. The first asexual propagation of 'KORelamba' was done by budding in July 2005 at the inventor's nursery in Offenseth-Sparrieshoop, Germany.

These initial and other subsequent propagations conducted in controlled environments demonstrate that 'KORelamba' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORelamba'.

DETAILED BOTANICAL DESCRIPTION

The following is a description of 'KORelamba', as observed growing in September 2014 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2010 are compared to 'KORelamba' in Chart 1.

CHART 1

| Characteristic | 'KORelamba' | 'KORcasima' |
|---|---|---|
| Petal count. | Double, with 30 to 35 petals. | Very double, with 70 to 80 petals. |
| Plant habit. | Upright. 120 to 135 cm (h) × 60 cm (w). | Bushy. 70 to 80 cm (h) × 60 to 70 cm (w). |
| Leaf size. | 130 to 140 mm (l) × 90 to 100 mm (w). | 125 mm (l) × 75 mm (w). |

Parents:

*Seed parent.*—An un-named seedling.

*Pollen parent.*—An un-named seedling.

Classification:

*Botanical classification.*—*Rosa hybrida* 'KORelamba'.

*Commercial classification.*—Floribunda rose.

FLOWER AND FLOWER BUD

Blooming habit: Recurrent.

Flower bud:

*Size.*—Upon opening, 20 mm in length from base of receptacle to distal end of bud and 15 mm diameter at its widest point.

*Calyx.*—Upon ¼ of opening, 20 mm in length from base of receptacle to distal end of bud and 15 mm diameter at its widest point.

*Bud form.*—Short. Globular.

*Bud color.*—As sepals first unfold, bud color is Red Group 53B. When ¼ open, the upper surface of petals is Red Group 53B, and the lower surface is Red-Purple Group 61B. Outermost petals are Red-Purple Group 61B with intonations of Yellow-Green Group 144A on the midrib.

*Sepals.*—Color: Upper surface Green Group 137B. Lower surface Green Group 137C. Size: Average 20 to 35 mm (l)×6 to 10 mm (w). Shape: Weak foliaceous appendages on three of the five sepals. Apex: Both cirrose and apiculate apices present. Base: Flat at union with receptacle. Quantity: Five. Surface texture: Upper side: Papillate. Lower surface: Hoary. Margins: Entire, with many stipitate glands. Stipitate glands: Abundant on margins and lower surface.

Flower bloom:

*Fragrance.*—Light.

*Duration.*—On the plant 6-8 days. Senesced petals drop away cleanly.

*Size.*—Large for a floribunda rose. When open, the average flower diameter is 85 mm and the average flower height is 40 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Red-Purple Group 61B. Inner Side: Red Group 46A. Innermost petals: Outer Side: Red-Purple Group 58A with intonations of White Group N155B along the midrib. Inner Side: Red Group 46A.

*Upon opening, basal petal spots.*—Size: 8 mm (l)×7 mm (w). Basal petal spot, outermost petals: Outer Side: Yellow Group 2C. Inner Side: Yellow Group 2D. Basal petal spot, innermost petals: Outer Side: Yellow Group 2C. Inner Side: Yellow Group 2C.

*After opening, petals.*—Outermost petals: Outer Side: Red-Purple Group 61B, with occasional intonations of White Group N155B along the midrib. Inner Side: Red Group 53B to 53C. Innermost petals: Outer Side: Red-Purple Group 60D with intonations of White Group N155B along the midrib. Inner Side: Red Group 53C.

*After opening, basal petal spots.*—Basal petal spot, outermost petals: Outer Side: White Group 155C. Inner Side: White Group 155C. Basal petal spot, innermost petals: Outer Side: White Group 155B. Inner Side: White Group 155B.

General tonality: On open flower Red Group 53B. No change in the general tonality at the end of the $6^{th}$ day. Afterwards, general tonality is Red-Purple Group N57B.

Petals:

*Petal count.*—Double. Approximately 30 to 35 petals under normal conditions.

*Petal reflex.*—Moderate, occurring as petals mature.

*Petal margin.*—Emarginate. With weak undulation.

*Petal shape.*—Obovate. Apex: Obtuse, emarginate. Base: Cuneate.

*Petal size.*—30 to 45 mm (l)×35 to 45 mm (w).

*Size of basal petal spot*.—Outer side: Medium. Inner side: Medium.

*Petal arrangement*.—Rosette. Not formal.

*Texture*.—Upper Side: Leathery. Lower Side: Leathery.

Petaloids:

*Petaloid count*.—Average of 6 to 10 per flower.

*Petaloid size*.—10 to 30 mm (l)×5 to 25 mm (w).

*Petaloid color*.—Inner side: Red Group 53B. Outer side: Red-Purple Group 61B with intonations of White Group N155B along the midrib.

*Petaloid texture*.—Upper Side: Smooth. Lower Side: Smooth.

*Margins*.—Emarginate, with some margins highly irregular.

*Petaloid shape*.—Most commonly obovate, with some petaloids highly irregular. Apex: Obtuse, emarginate. Base: Attenuate.

Reproductive organs:

*Pistils*.—Abundant. Approximately 80 present. Stigmas: Size: 1 mm (l)×1 mm (w). Location: Equal in position to anthers. Color: Greyed-Orange Group 163C. Styles: Length: About 8 to 10 mm long. Color: Red-Purple Group 58B.

*Stamens*.—Approximately 100 on average and regularly arranged. Anthers: Size: Average 2 mm (l)×1 mm (w). Color: Greyed-Orange Group 165A. Pollen: Generally present. Color: Greyed-Orange Group 163A. Filaments: Color: White Group 155A. Length: 8 to 10 mm.

Receptacle:

*Surface*.—Glaucous.

*Color*.—Yellow-Green Group 144A.

*Shape*.—Urn-shaped.

*Texture*.—Glabrous.

*Size*.—5 mm (h)×8 mm (w).

Pedicel:

*Surface*.—With limited numbers of fine hairs and moderate numbers of stipitate glands.

*Length*.—65 to 100 mm average length.

*Diameter*.—3 to 4 mm average diameter.

*Color*.—Yellow-Green Group 144B.

*Strength*.—Strong.

*Texture*.—Papillate.

Peduncle:

*Surface*.—Lacking fine hairs and stipitate glands.

*Length*.—40 to 60 mm average length.

*Diameter*.—3 to 4 mm average diameter.

*Color*.—Yellow-Green Group 144A, with intonations of Red-Purple Group 60A.

*Strength*.—Strong.

*Texture*.—Glabrous.

*Borne*.—Inflorescence type: Corymb. Inflorescence length: 20-30 cm×18-22 cm wide. Multiple flower buds per flower shoot, generally 1 to 3. Flowers held upright. Flowering laterals are present, with generally 1 to 3 flower buds per lateral.

THE PLANT

Growth: Moderately vigorous.

Plant habit: Upright. When grown as a field plant, the average plant height is 120 to 135 cm and the average plant width is 60 cm.

Stems:

*Stem size*.—Length: Variable 12 to 24 inches. Diameter: Variable 4 to 6 mm.

*Stem color*.—Young wood: Yellow-Green Group 145A. Older wood: Yellow-Green Group 144A.

*Intonations*.—Red-Purple Group 60A, on immature stems, absent on mature wood.

*Stem surface texture*.—Young wood: Smooth. Older wood: Smooth.

Prickles: Present.

*Incidence*.—Average of 6 large prickles and 20 small to medium prickles per each 10 cm of stem.

*Size*.—Average length, large prickles: 7 to 9 mm. Average length, medium prickles: 3 mm. Average length, small prickles: 1 mm.

*Color*.—Immature prickles: Yellow-Green Group 145C. Mature prickles: Yellow-Green Group 145A.

*Shape*.—Large prickles: Deeply concave. Small and medium prickles: Linear.

*Anthocyanin*.—Color: Red-Purple Group 60A. Covers immature prickles, present at base and along upper edge of mature prickles.

Leaves: Normally 5 leaflets on normal leaves in middle of the stem.

*Venation pattern*.—Pyramidal net pattern.

*Leaf size*.—130 to 140 mm (l)×90 to 100 mm (w).

*Abundance*.—Very abundant.

Leaflets:

*Size*.—Average size of the terminal leaflet is 55 mm (l)×40 mm (w).

*Shape*.—Overall: Ovate. Base: Obtuse. Apex: Acute.

*Margins*.—Finely serrated.

*Surface*.—Upper side of leaflet: Semi-glossy. Under side of leaflet: Matte.

*Texture*.—Upper side of leaflet: Leathery. Under side of leaflet: Leathery.

*Color, mature foliage*.—Upper Leaflet Surface: Yellow-Green Group 147A. Lower Leaflet Surface: Yellow-Green Group 146A.

*Color, juvenile foliage*.—Upper Leaflet Surface: Yellow-Green Group 147A. Lower Leaflet Surface: Yellow-Green Group 146C.

*Anthocyanin intonation*.—Red-Purple Group 60A. Location: Covers juvenile foliage, most prominent on underside. Absent on mature foliage.

*Arrangement*.—Odd pinnate.

*Venation*.—Reticulate.

Stipules:

*Size*.—25 mm (l)×6 mm (w).

*Stipule color*.—Yellow-Green Group 145A along midrib, Yellow-Green Group 146A near margins.

*Anthocyanin*.—Red-Purple Group 60A, present on midrib.

*Stipitate glands*.—Abundant on margins.

*Margins*.—Serrated.

*Texture*.—Glabrous.

*Shape*.—Apex: Apiculate. Base: Winged.

Petiole:

*Length*.—Average 20 to 30 mm.

*Diameter*.—Average 1.5 mm.

*Petiole color*.—Upper side: Yellow-Green Group 146A. Underneath: Yellow-Green Group 146C.

*Margins*.—With limited numbers of stipitate glands.

*Anthocyanin*.—Red-Purple Group 60A, present along midrib.

*Prickles*.—Several small prickles present underneath.
*Stipitate glands*.—Limited numbers of stipitate glands present on margins and underside.
*Texture*.—Papillate.

Petiole rachis:
*Length*.—Average 20 to 30 mm.
*Diameter*.—Average 1 to 1.5 mm.
*Color*.—Yellow-Green Group 146A.
*Anthocyanin*.—Red-Purple Group 60A present along midrib and at leaflet attachments.
*Prickles*.—A few small prickles underneath.
*Stipitate glands*.—Limited numbers of stipitate glands on margins.

Hips/seed formation: None observed.

Winter hardiness: To date, the variety has been grown successfully in USDA Hardiness Zones 5-9.

Disease resistance: Above average resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

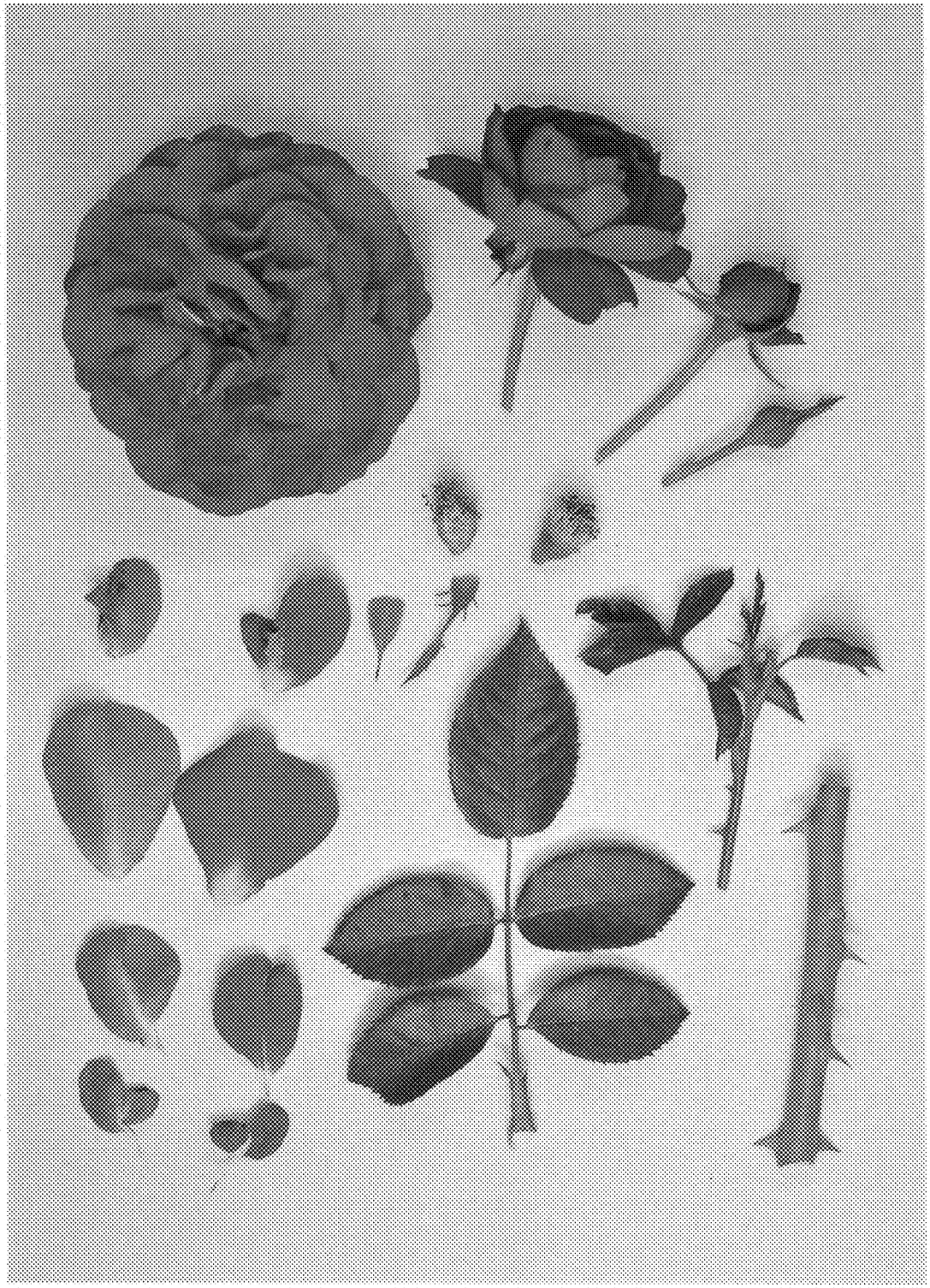

* * * * *